United States Patent [19]

Page et al.

[11] Patent Number: 4,943,282

[45] Date of Patent: Jul. 24, 1990

[54] SHIELD FOR DEVICES CAPABLE OF PENETRATING SKIN

[76] Inventors: Mary J. Page, 4634 French Meadow, San Antonio, Tex. 78250; Benton W. Hamilton, 13403 Townwood, Houston, Tex. 77045; Bruce L. Skiles, 15 Charleston Park, No. 714, Houston, Tex. 77025; Robert V. Reinhart, Jr., 2303 Moss Ter., San Antonio, Tex. 78232

[21] Appl. No.: 311,044

[22] Filed: Mar. 13, 1989

Related U.S. Application Data

[62] Division of Ser. No. 181,387, Apr. 14, 1988, abandoned.

[51] Int. Cl.5 .............................................. A61M 5/32
[52] U.S. Cl. ..................................... 604/198; 604/263
[58] Field of Search .............. 604/198, 263, 195, 192, 604/187

[56] References Cited

U.S. PATENT DOCUMENTS

| 4,425,120 | 1/1984 | Sampson et al. | 604/198 |
| 4,723,943 | 2/1988 | Spencer | 604/198 |
| 4,758,231 | 7/1988 | Haber et al. | 604/263 X |

Primary Examiner—John D. Yasko
Attorney, Agent, or Firm—John R. Merkling

[57] ABSTRACT

A shield to selectively surround a needle or other sharp protrusion on a medical device, such as a syringe, to inhibit accidental injury.

3 Claims, 1 Drawing Sheet

SHIELD FOR DEVICES CAPABLE OF PENETRATING SKIN

This application is a division of Ser. No. 181,387, filed Apr. 14, 1988 now abandoned.

FIELD OF INVENTION

This invention relates principally, but not exclusively, to medical devices but particularly to apparatus for providing a shield to surround a needle or other sharp protrusion on a device and thus to inhibit accidental injury.

BRIEF SUMMARY AND OBJECTS OF THE INVENTION

In brief, summary the present invention comprises a moveable shield slidably attached to the body of a syringe or other device and capable of being positioned around a needle or other sharp protrusion to inhibit accidental injury by a user. The shield may cover the needle temporarily or permanently, depending on the application of the device. Moreover, the shield may be sized to receive a second device or container, without retraction from surrounding the needle, thus permitting the contents of the syringe to be discharged into the container with reduced risk of injury.

With the foregoing in mind, it is a primary object of the present invention to provide a slidable shield for syringes and the like which will reduce the risk of accidental injury from needles and the like attached to such syringes.

A further important object is the provision of the shield which may be temporarily positioned to enclose a needle on a syringe.

Another important object is to provide a shield for a syringe or similar object which will permanently enclose a needle on a syringe. Another dominate object is the provision of a shield wherein the contents of a syringe can be discharged into a second medical device with retracting the shield.

These and other objects and features of the present invention will be apparent from the detailed description taken with reference to the accompanying drawings.

DETAILED DESCRIPTION OF THE ILLUSTRATED EMBODIMENT

Figure 1:
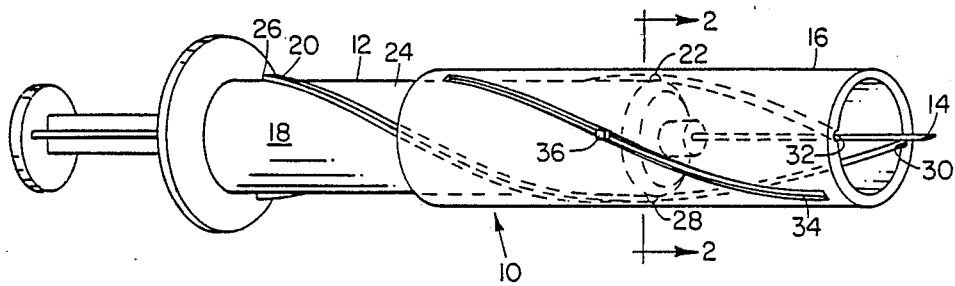
FIG. 1 is a perspective drawing of a syringe and shield according to the present invention.
Figure 2:
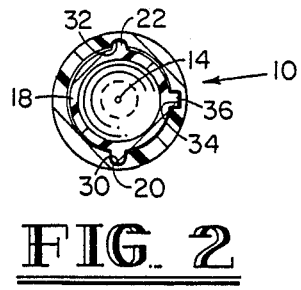
FIG. 2 is a cross-sectional view of the shield and syringe of FIG. 1, taken along line 2—2.

Reference is now made to the drawings wherein like numerals are used to designate like parts throughout. FIG. 1 illustrates a presently preferred embodiment of the present invention generally designated 10. The apparatus comprises a medical device 12, such as a syringe, having an appendage, such as a needle 14, capable of accidentally injuring the user or injecting foreign substances into the body of a user. The apparatus 10 further comprises a tubular shield 16 which slidably engages a body 18 of the syringe 12. In the embodiment illustrated in FIG. 1, the body 18 of the syringe 12 further comprises two opposing ridges 20, 22 which twist around an outer surface 24 of the syringe body 18. In the preferred embodiment, each ridge, such as ridge 20, traverses one-half of the circumference of the syringe body 18, clockwise from a back end 26 to a front end 28 thereof. The ridges 20, 22 slidably engage corresponding grooves 30, 32 in the shield 16. The shield is also provided with a slot 34, equidistant between the two grooves 32, 30. The slot 34 slidably engages a stop pin 36 which is affixed to the outer wall 18 of the syringe 12.

When the apparatus 10 is in use, the shield 16 is retracted away from the needle 14 by rotating the shield 16 about the body 18 of the syringe 12. The shield 16 is engaged by rotating the shield 16 about the body 18 of the syringe 12 and pushing the shield 16 forward to enclose the needle 14. The shield 16 is held in position by frictional forces and is prevented from coming off the syringe 12 by the stop pin 36 in the groove 34.

Figure 3A:
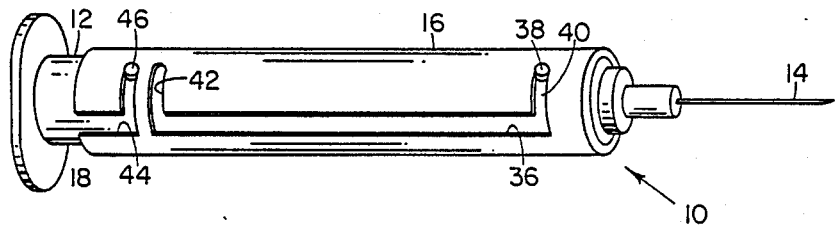
FIG. 3A is an alternative embodiment of a shield according to the present invention.
Figure 3B:
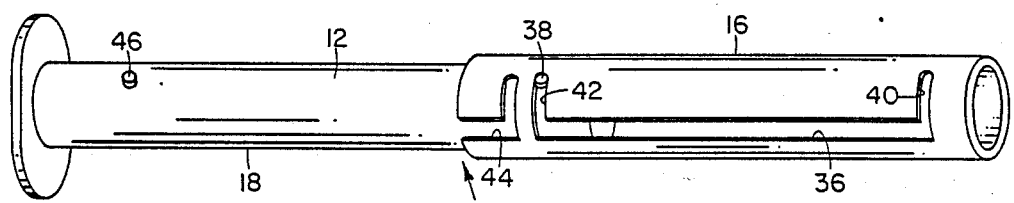
FIG. 3B is a perspective drawing of the shield and syringe of FIG. 3A, showing the shield extended.

A second embodiment of the invention is disclosed in FIGS. 3A and 3B. The shield 16 is provided with a U-shaped slot 36 along substantially the entire length of the shield 16. A first pin 38, affixed to the body 18 of the syringe 12, slidably engages the slot 36. A first leg 40 of the slot 36 engages the pin 38 when the shield 16 is in a retracted position. The shield 16 can be manipulated into an extended position covering the needle 14 by rotating and pushing the shield forward to bring the pin 38 into a second leg 42 of the slot 36. In this embodiment, the shield 16 is more securely positioned over the needle 14 and the user does not rely solely on frictional forces to prevent retraction of the shield 16.

The shield 16 may also be provided with an L-shaped slot 44 which slidably engages a second pin 46. The L-slot 44 and pin 46 serve to limit excessive twisting of forces which might otherwise shear off the first pin 38.

Figure 4A:
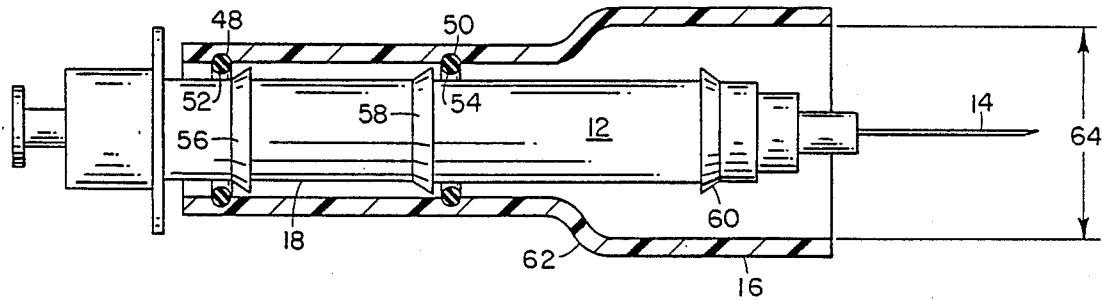
FIG. 4A is a cross-sectional representation of an alternative embodiment of a shield according to the present invention with a permanent locking feature.
Figure 4B:
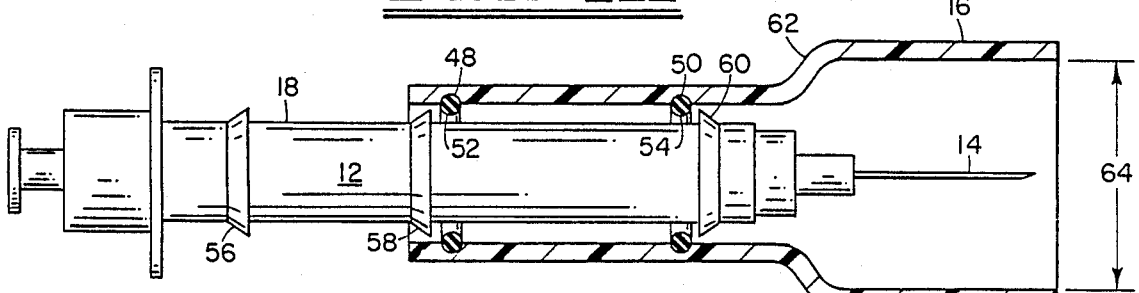
FIG. 4B is a cross-sectional view of the shield and syringe of FIG. 4A, with the shield enclosing a needle on the syringe.

A third embodiment of the present invention is disclosed in FIGS. 4A and 4B. FIG. 4A shows a cross-section of the shield 16. The shield 16 has two parallel concentric grooves 48, 50 which contain a first rubber O-ring 52 and a second rubber O-ring 54, respectively. The O-rings 52, 54 slidably engage the body 18 of the syringe 12. When the sleeve 16 is retracted, the first O-ring 52 is positioned behind a first stop collar 56. In the illustrated embodiment, the first stop collar 56 comprises a wedge shaped ring which inhibits forward motion of the sleeve 16 along the syringe 12, but does not prevent forward motion. The second O-ring 54 engages a collar 58, similar to collar 56 and which prevents the sleeve 16 from sliding further backward along the syringe 12. When the sleeve 16 is slid forward to cover the needle 14, the first O-ring 52 is forced over both the collar 56 and the collar 58. The second stop collar 58 then engages the first O-ring 52 to prevent the sleeve 16 from being retracted. In that position, the second O-ring 54 engages a third stop collar 60 which prevents the sleeve 16 from sliding further forward along the syringe 12.

As illustrated in FIG. 4A and FIG. 4B, the sleeve 16 may have an expanded diameter at a forward portion 62 thereof. An inside diameter 64 of the sleeve 16 may be adjusted to accommodate the insertion of medical devices, such as a stoppered test tube for receiving blood samples, without retracting the shield 16 and exposing the needle 14.

The invention may be embodied in other specific forms without departing from the spirit or essential characteristics thereof. The present embodiment is therefore considered in all respects to be illustrative and not restrictive, the scope of the invention being indicated by the appended claims rather than by the foregoing description and all changes which come within the meaning and range of equivalency of the claims are therefore intended to be embraced therein.

What is claimed and desired to be secured by Unites States Letters of Patent is:

1. An apparatus for inhibiting accidental injury to a user of a device having a part thereof capable of penetrating skin of said user, said apparatus comprising a sleeve slidably and rotatably engaging a portion of said device adjacent to said penetrating part;

first means connected to said sleeve for retaining said sleeve at a first position on said portion of said device whereby the penetrating part is exposed, and second means connected to said sleeve for retaining said sleeve at a second position on said portion of said device whereby a part of the sleeve substantially surrounds the penetrating part, the first and second sleeve retaining means comprising at least one groove inscribed along an axial length of an inside surface of said sleeve, each groove being substantially circumferentially equidistant from any other groove, at least one ridge carried on said adjacent portion of said device, each ridge slidably engaging one of the at least one grooves, at least one slot along the axial length of said tube, each slot being substantially circumferentially equidistant from the at least one groove, and at least one peg carried on said penetrating part adjacent portion of said device, each peg slidably engaging one of the at least one slots.

2. An apparatus according to claim 1 wherein the at least one groove is curved along a length thereof.

3. An apparatus according to claim 2 wherein the apparatus further comprises means connected to the sleeve for releasably engaging a container for receiving a discharge from the device while the penetrating part is substantially surrounded by the sleeve.

* * * * *